United States Patent
Anderson et al.

(10) Patent No.: US 7,867,511 B2
(45) Date of Patent: Jan. 11, 2011

(54) ABUSE POTENTIAL REDUCTION IN ABUSABLE SUBSTANCE DOSAGE FORM

(75) Inventors: Carter R. Anderson, Inver Grove Heights, MN (US); Russell L. Morris, Lindstrom, MN (US)

(73) Assignee: Travanti Pharma Inc., Mendota Heights, MN (US)

( * ) Notice: Subject to any disclaimer, the term of this patent is extended or adjusted under 35 U.S.C. 154(b) by 747 days.

(21) Appl. No.: 10/763,628

(22) Filed: Jan. 23, 2004

(65) Prior Publication Data

US 2005/0163717 A1 Jul. 28, 2005

(51) Int. Cl.
*A61K 9/70* (2006.01)
*A61F 13/00* (2006.01)

(52) U.S. Cl. .................. 424/449; 514/282; 514/622

(58) Field of Classification Search ......... 424/447–449, 424/760, 484–486; 602/41, 48, 54; 206/204, 206/461, 538
See application file for complete search history.

(56) References Cited

U.S. PATENT DOCUMENTS

| | | | |
|---|---|---|---|
| 4,588,580 A * | 5/1986 | Gale et al. ................. | 424/449 |
| 5,149,538 A * | 9/1992 | Granger et al. ............. | 424/449 |
| 5,236,714 A * | 8/1993 | Lee et al. .................... | 424/449 |
| 5,597,617 A | 1/1997 | DeLiso et al. | |
| 5,899,856 A * | 5/1999 | Schoendorfer et al. ...... | 600/362 |
| 6,261,595 B1 * | 7/2001 | Stanley et al. ............... | 424/449 |
| 6,261,596 B1 * | 7/2001 | Li et al. ...................... | 424/450 |
| 6,279,736 B1 * | 8/2001 | Hekal ......................... | 206/204 |
| 6,660,901 B2 * | 12/2003 | Church ....................... | 602/48 |
| 2002/0187183 A1 | 12/2002 | Becher et al. | |
| 2003/0068392 A1 * | 4/2003 | Sackler ....................... | 424/760 |
| 2004/0146547 A1 * | 7/2004 | Marcenyac et al. ......... | 424/449 |
| 2006/0110080 A1 | 5/2006 | Thomas et al. | |
| 2007/0250339 A1 | 10/2007 | Mallett et al. | |
| 2009/0131732 A1 | 5/2009 | Day | |

OTHER PUBLICATIONS

Joseph Greensher, Howard C Mofensno, Thomas R. Caraccio, Ascendency of the Black Bottle (Activated Charcoal), Pediatrics, vol. 80(6), 949-951, 1987.*
Yerasi et al, American Journal Health-System Pharm., *Disposal of Used Fentanyl Patches*, vol. 54, Jan. 1, 1997, pp. 85-86.
Marquardt et al, The Annals of Pharm., *Fentanyl Remaining in a Transdermal System Following Three Days of Continuous Use*, vol. 29, Oct. 1995, pp. 969-.
Zambaux et al, The Annals of Pharm., *Validation d'une méthode d'inactivation du fentanyl dans les dispositifs usagés de Durogésic*, vol. 58, (2000) pp. 176-179.

* cited by examiner

*Primary Examiner*—Michael G Hartley
*Assistant Examiner*—Jagadishwar R Samala
(74) *Attorney, Agent, or Firm*—Nikolai & Mersereau, P.A.; C.G. Mersereau

(57) ABSTRACT

The potential for substance abuse involving residual amounts of abusable substances remaining in used skin-worn patches is reduced by the provision of a system and method for combining the abusable substance with a separate anti-abuse substance agent as part of a removal or disposal procedure.

8 Claims, 3 Drawing Sheets

ABUSE POTENTIAL REDUCTION IN ABUSABLE SUBSTANCE DOSAGE FORM

BACKGROUND OF THE INVENTION

I. Field of the Invention

The present invention relates generally to transdermal dosage forms for administering substances of a class typically subject to abuse to the body of a patient and, particularly, to reducing the potential for abuse related to the use of such devices. More particularly, the invention involves the use of binding agents to immobilize and prevent extraction of amounts of abusable substances remaining in transdermal patch devices after initial therapeutic transdermal administration to a patient. Other techniques are also included.

II. Related Art

The temptation and potential for abuse by ingestion, injection, etc. of narcotics and other controlled substances is well known. This widespread abuse issue is exemplified by the problems associated with fentanyl, the widely used potent synthetic narcotic drug. Abuse of this drug has become a significant issue among anesthesiologists and other hospital workers.

Of particular interest is the potential for abuse associated with transdermal patch technology (passive or active) which is a preferred method of administration because it can eliminate the need for repeated oral dosing. Unfortunately, with transdermal patches, significant amounts of drug compound remain in the patches after patients have worn them for the prescribed period of time. The need for this excess amount of drug is well known, it is required to insure an adequate driving force in the transdermal application for the full wear time period. For example, in a published test of Duragesic (trademark of Johnson & Johnson) patches worn for the full 72-hour wear period, 28-84.4% of the original loading of fentanyl still remained in the patches. The authors of the study concluded that the residual dosage represented amounts sufficient for abuse and misuse and was even potentially lethal. (Marquardt et al, Ann Pharmacother, 1995, 29:969-71). Using the 2002 published consumption rate of fentanyl, an estimated 50 million or more abusable, toxic dosages of fentanyl are released into the environment annually.

Upon recognizing the need to deactivate residual fentanyl following the wearing of transdermal patches, researchers in a published study recommended that used patches be immersed in heated concentrated hydrochloric or sulfuric acid (Zambaux et. al. Ann Pharm Fr 2000, 58: 176-179). This method was found to deactivate the residual. fentanyl by a hydrolysis chemical reaction. A significant disadvantage of this method is that it requires very hazardous materials and procedures.

Another approach to the reduction of abuse potential in transdermal drug administration is found in U.S. Pat. No. 5,236,714. That document discloses the combination of the drug with a co-formulated antagonist agent that is present in a form not releasable in the dosage form, but one which releases to prevent abuse of the composition by certain other routes of administration. Thus, the co-formulated antagonist does not penetrate transdermally, but would be co-extracted during an attempt to extract the abusable material as by using solvents or by removing and ingesting the combination. One disadvantage to this aproach resides in the shelf-life complications associated with co-formulation of two active pharmaceutical ingredients in a transdermal patch. Another significant limitation to this approach is that a used patch can still be abused with transdermal wear.

There still remains a need, then, for a safe and effective means of preventing abuse involving excess amounts of drugs, particularly opioid-type drugs associated with transdermal administration of such materials that protects against abuse by transdermal wear without requiring hazardous materials.

SUMMARY OF THE INVENTION

By means of the present invention there is provided a system and method for reducing the potential for substance abuse in skin-worn transdermal patch devices containing residual amounts of abusable substances after removal of the patch devices from a first user. The invention involves the use of a separate anti-abuse substance which may be a binding agent which immobilizes and deactivates the abusable substance on contact thereby reducing the potential for abuse. The anti-abuse substance may also contain an antagonist or irritant compound or, in certain cases, consist of an antagonist or irritant compound as will be described below. The abuse prevention system of the present invention is generally associated with the removal and disposal of skin-worn patches and may take any of several forms.

Preferred binding compositions include those binding agents which may be absorbents for the abusable material. These agents immobilize the abusable substance and precludes future separation by normally available means. Activated carbon has been found to be a material particularly suitable for the adsorption of opioid compounds including synthetic opioids such as fentanyl. Thus, contacting these compounds with a suitable binding agent has been found to thereafter prevent extraction by normal solvents and other means readily available to prospective abusers.

One form of a system for reducing potential substance abuse in skin-worn transdermal patch devices containing residual amounts of abusable substances in accordance with the present invention includes a disposable container or pouch which has an opening configured to receive a skin-worn patch device after removal from a patient at the conclusion of the normal course of dosage administration. The container or pouch is provided with an amount of an anti-abuse substance normally in the form of a binding agent selected for use with the particular abusable substance contained in the patch and is located in the container or pouch. When a skin-worn patch device is properly inserted into the container or pouch, contact between the portion of the patch containing the abusable substance and the binding agent will be made, thereby immobilizing and deactivating the abusable substance. A closure device for closing the container or pouch is also provided so that the container can also provide a closed system for disposing of the used skin-worn patch. The closure system may include an adhesive seal or zip lock to seal the patch in the container.

In an alternative embodiment of the invention, a layer of absorbent material such as activated carbon is provided in the patch itself separated from the layer containing the active ingredient by a lightly adhering separation membrane. The separation membrane remains in place during the initial application and wearing of the patch but is provided with an extension or connecting section which includes an amount of adhesive near the end and which adhesively adheres to the skin of the patient at the time the patch is applied. Removal of the patch leaves the extension temporarily adhered to the skin and so causes the extension or connecting device to pull on and remove the separator membrane from between the layer of anti-abuse substance or absorbent material and the layer containing the active ingredient as the patch is removed from the patient so that the two are brought into contact and the remaining active ingredient is immobilized or absorbed by the binding agent or absorbent, thereby rendering the remaining dosage harmless.

It should be recognized, then, that the primary objective of this invention lies in the prevention of drug-abusers from recovering drugs into an abusable form, from a used transdermal patch. Accordingly, it has been discovered that a binding agent, such as activated carbon, can prevent users from recovering drugs with use of commonly available solvents such as water, ethanol and mixtures thereof. However, some abusers may have access to less common solvents, some of which might be effective in separation of the drug from the binding agent.

An option that can be selectively utilized in the present invention to further prevent abuse with the use of extraordinary solvents, is the incorporation of either antagonist or irritant compounds into a portion of the binding agent mix that will also be extracted. In this case, when an abuser attempts to remove the drug from the binding agent, the antagonist and/or irritant is co-extracted along with the drug. As used herein, an antagonist for an abusable substance is a compound or composition which acts upon or affects the user to essentially diminish or prevent the pharmacological effects of the abusable subject or greatly delays such affects. As used herein, an irritant refers to any substance that causes inflammation following immediate, prolonged, or repeated contact with skin or mucous membranes. Examples of suitable protection agents include, without limitation, naloxone or naltrexone as antagonists and capsaicin or epicac as irritants.

In accordance with the invention, it is also possible to simply use a separate antagonist and/or irritant layer in the place of a binding agent. An advantage of this approach as compared to prior concepts such as that of U.S. Pat. No. 5,236,714, cited above, is that the antagonist and/or irritant layer is designed to be kept separated from the drug during storage and wear periods, thereby presenting an advantage from a shelf life stability perspective. However, the preferred deactivation method is one that additionally or principally incorporates a binding mechanism.

BRIEF DESCRIPTION OF THE DRAWINGS

In the drawings wherein like numerals depict like parts throughout the same.

DETAILED DESCRIPTION

Figure 1:
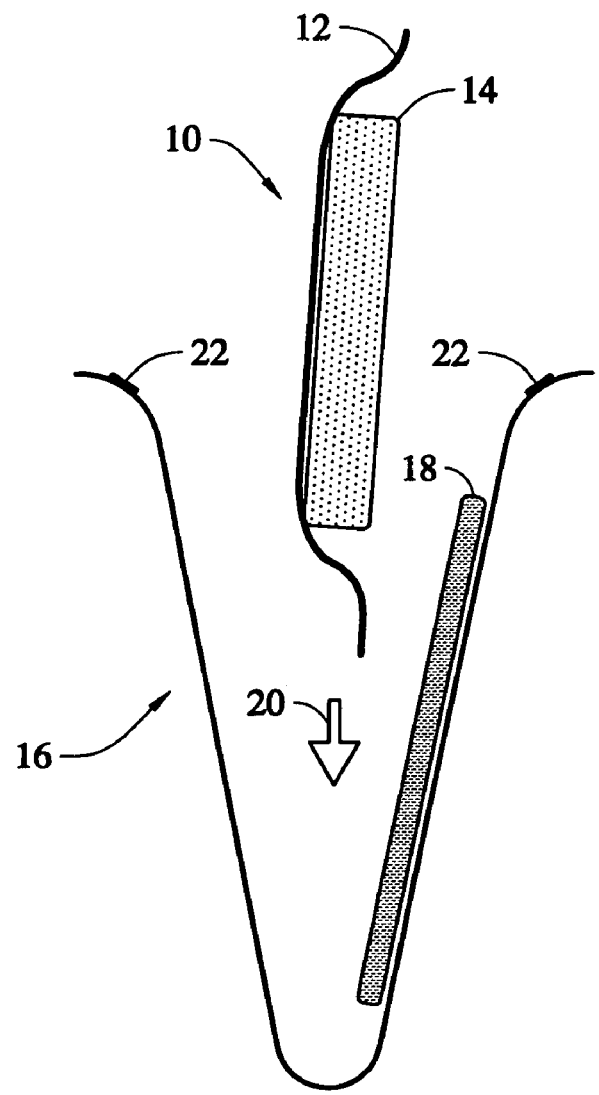
FIG. 1 is a simplified schematic view of one embodiment of the invention showing a patch and container system with parts omitted for clarity.

FIG. 1 depicts a skin-worn patch 10 of a class utilized with transdermal delivery of an abusable substance such as an opioid. The patch is depicted generally by 10 and includes a skin fastening adhesive-containing layer 12 and an opioid-containing layer designed to contact the skin at 14. A disposal container or pouch designed to accompany the skin-worn patch 10 is shown generally by the reference character 16 and includes a layer of absorbent material 18 attached to one side of the container 16 in the manner such that insertion of the used skin-worn patch 10 as is shown by the arrow 20 with the opioid layer 14 facing the adsorptive material 18, ensures that contact will occur between the layers 14 and 18, thereby adsorbing and deactivating the opioid from layer 14. The container 16 is also provided with a means of sealing the patch 14 inside such as exemplified by adhesive strips 22 on each side of the container. In this manner, the container 16 containing the used patch 14 may then be thrown away with the knowledge that the opioid material contained in the layer 14 of the skin-worn patch 10 has been successfully deactivated by the adsorptive material in the layer 18. In the case of opioids, this is preferably activated carbon.

Figure 2A:
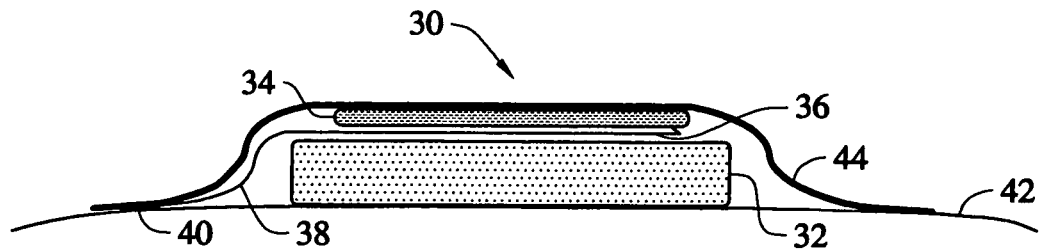
FIGS. 2a and 2b are simplified schematic drawings that depict an alternate embodiment of the abuse potential reducing system of the invention.
Figure 2B:
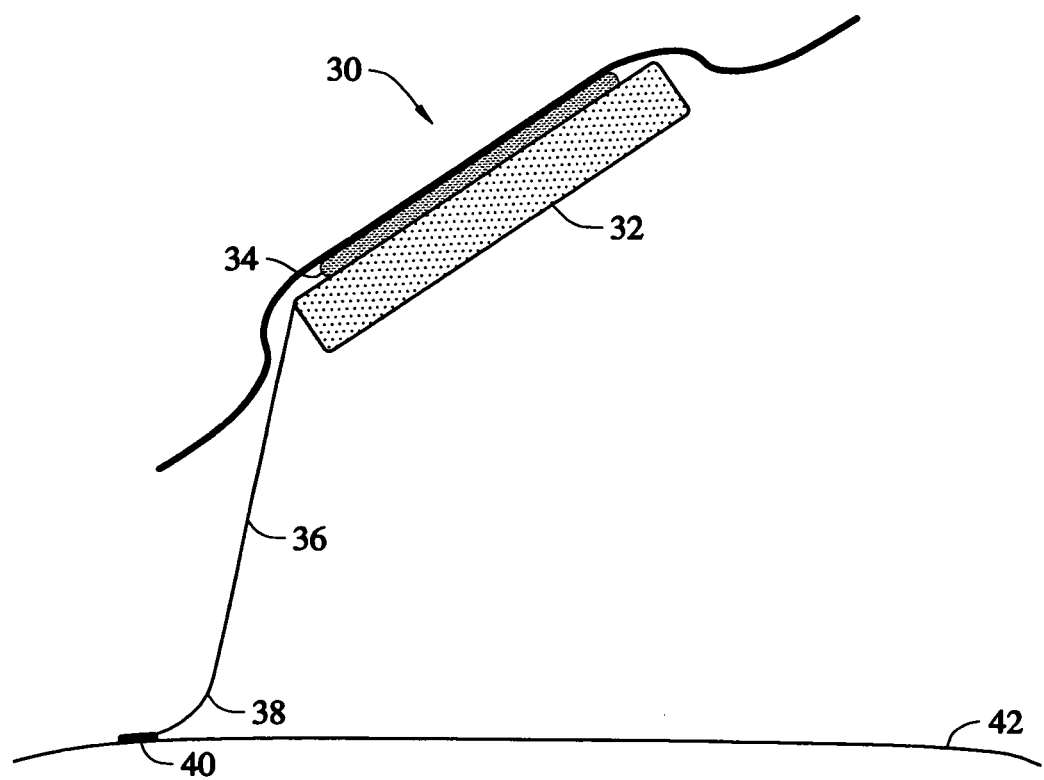

The second embodiment is shown in FIGS. 2a and 2b. Those drawings illustrate a simplified schematic representation of a skin-worn patch 30 for the transdermal delivery of a therapeutic drug material such as an opioid contained in a layer 32. A layer containing an amount of absorbent material, such as activated carbon, is shown at 34. In FIG. 2a, the patch 30 is depicted as it would appear when applied to the skin of a patient and as it would appear during administration of the abusable substance to the patient. The patch is provided with a lightly adhering or releasable separation membrane 36 which separates the substance to be administered in layer 32 from the absorbent material in layer 34. The membrane 36 is attached to or is provided with an integrally formed connector shown at 38 which contains an amount of adhesive 40 which causes the connector 38 to adhere to the skin of a patient shown at 42. The normal patch adhesive overlayer which attaches the patch to the skin is shown at 44.

FIG. 2b depicts the patch 30 as it is being removed from the skin 42 of a patient. Note that the removal of the adhesive layer 44 with the patch leaves the adhesive 40 with connector 38 still attached to the skin. In this manner, the connector 38 causes the separator membrane 36 to be pulled out from between the layers 32 and 34 thereby allowing the absorbent material in layer 34 to contact the remaining amount of active abusable substance in layer 32 deactivating the remaining amounts of abusable substance in the patch.

Figure 3:
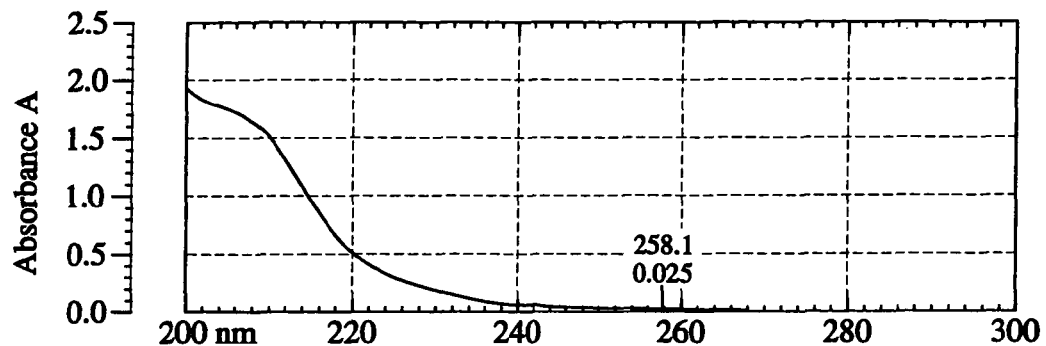
FIG. 3 is a plot showing a UV/VIS spectrophotometry scan of a 37.7 mg/l solution of fentanyl citrate showing absorption from 200-240 nm.

FIG. 3 depicts a plot of a UV/VIS spectrophotometry scan of a 37.7 mg/l solution of fentanyl citrate. The absorption from 200-240 nm is due to the fentanyl citrate present in the solution, and the magnitude of the absorbance is directly related to the dissolved concentration of that compound. It is readily seen that the concentration of the drug is significant.

Figure 4:
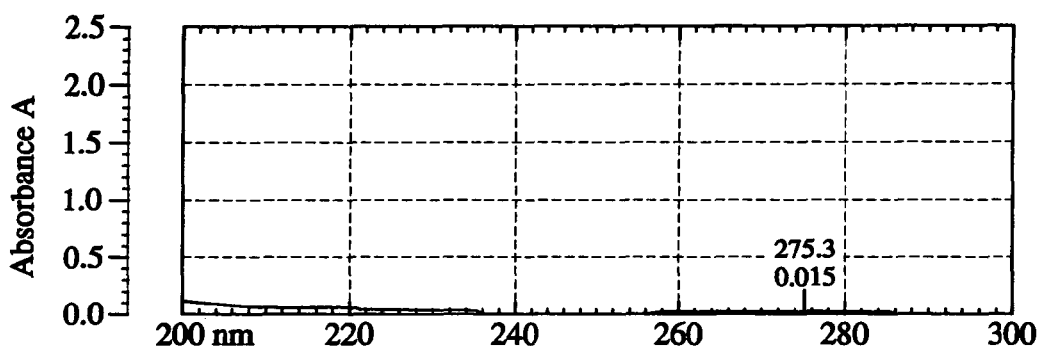
FIG. 4 is a UV/VIS spectrophotometry scan plot of the solution of FIG. 3, after 5 minutes of contact with activated carbon.

FIG. 4 represents a second UV/VIS spectrophotometry scan plot of the solution of FIG. 3 after 5 minutes of contact with activated carbon. Note the dramatic reduction in the amount of absorption from 200-240 nm. The data shows that an estimated 97% of the fentanyl citrate had been removed from solution by 5 minutes of contact with activated carbon. Only 11 micrograms from the original content of 377 micrograms of fentanyl citrate was remaining in solution.

The activated carbon utilized to adsorb the fentanyl citrate from the solution of FIG. 3 was then taken and placed in a 50% ethanol/water solution in an attempt to redissolve the adsorbed fentanyl citrate.

Figure 5:
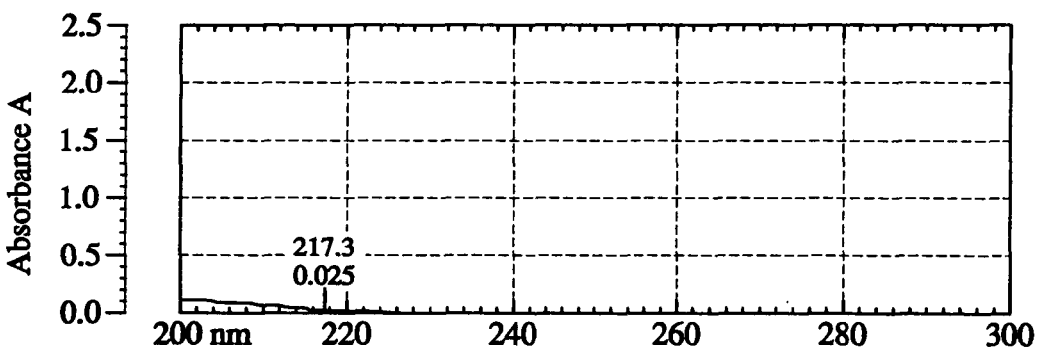
FIG. 5 is a UV/VIS spectrophotometry scan plot of a 50% ethanol solution utilized to attempt to extract adsorbed fentanyl citrate from the activated carbon used to adsorb the fentanyl citrate in FIG. 4.

The plot of FIG. 5 represents another UV/VIS spectrophotometry scan of the 50% ethanol solution from which it appears that recovery of fentanyl citrate in the 50% ethanol solution was extremely low, i.e., less than 5% of the drug was recovered. This indicates that the adsorption of the drug onto the carbon was not only almost complete, but also very tenacious. Of the 366 micrograms of fentanyl citrate that was bound, only 13 micrograms was successfully separated in the attempted extraction process.

It should further be noted that the layer of absorbent material 18 in FIG. 1 and the layer 34 of absorbent material in FIGS. 2a and 2b can be selectively provided with an antagonist and/or an irritant material that goes into solution with the opioid or other abusable drug of interest in order to provide further means of abuse protection. In those cases where abusers have access to less commonly available solvents, which could possibly be used to separate the drug of interest from the binding agent, the antagonist and/or irritant compounds serve as added abuse resistance protection. It is also contemplated that under some circumstances antagonist and/or irritant compounds might replace the binding agent entirely as the active anti-abuse substance or ingredient of the layers 18 and 34.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A disposal system for a skin-worn transdermal patch device containing residual amount of an abusable opioid substance after use thereof on a patient, said system comprising:
   (a) a disposal container separate from and independent of said skin-worn patch device and having an opening therein for receiving said skin-worn patch device;
   (b) a deactivation system in said container comprising material that deactivates and renders unusable said abusable opioid substance on contact, comprising:
      (1) a first amount of carbon in an activated state in a quantity sufficient to bind said abusable opioid substance in said patch;
      (2) a second amount of carbon that has been pre-incorporated with a species that is releasable from said second amount of carbon upon solvent extraction and wherein said species is selected from the group consisting of capsaicin, ipecac, naloxone and naltrexone and combinations thereof such that said species remains with said abusable opioid substance upon extraction thereby rendering said abusable opioid substance unusable; and
   (c) closure device for closing said disposal container thereby capturing said skin-worn patch device.

2. A system as in claim 1 wherein said container is in the form of a flexible pouch.

3. A system as in claim 1 wherein said closure device includes an adhesive seal.

4. A system as in claim 2 wherein said closure device includes an adhesive seal.

5. A system as in claim 1 wherein said opioid abusable substance comprises fentanyl.

6. A disposal system as in claim 1 wherein extraction solvents are water, ethanol and combinations thereof.

7. A disposal system as in claim 1 wherein said species includes capsaicin.

8. A disposal pouch for the deactivation of a used opioid transdermal patch comprising a deactivation system in said container comprising material that deactivates and renders unusable said abusable opioid substance on contact, comprising:
   (a) a first amount of carbon in an activated state in a quantity sufficient to bind said abusable opioid substance in said patch;
   (b) a second amount of carbon that has been pre-incorporated with a species that is releasable from said second amount of carbon upon solvent extraction and wherein said species is selected from the group consisting of capsaicin, ipecac, naloxone and naltrexone and combinations thereof such that said species remains with said abusable opioid substance upon extraction thereby rendering said abusable opioid substance unusable; and
   (c) a container in the form of a pouch.

* * * * *